United States Patent
Tucker et al.

(10) Patent No.: US 8,609,425 B2
(45) Date of Patent: Dec. 17, 2013

(54) DETERMINATION OF NITRATE/NITRITE CONCENTRATION IN WATER BY QUANTITATIVE PHOTOCHEMICAL REDUCTION USING $NH_4Cl$ AND EDTA

(75) Inventors: Scott A. Tucker, Fort Collins, CO (US); Lynn M. Egan, Loveland, CO (US)

(73) Assignee: Hach Company, Loveland, CO (US)

( * ) Notice: Subject to any disclaimer, the term of this patent is extended or adjusted under 35 U.S.C. 154(b) by 37 days.

(21) Appl. No.: 12/853,154

(22) Filed: Aug. 9, 2010

(65) Prior Publication Data

US 2011/0212533 A1 Sep. 1, 2011

Related U.S. Application Data

(60) Provisional application No. 61/232,298, filed on Aug. 7, 2009.

(51) Int. Cl.
*G01N 33/00* (2006.01)
*G01N 21/78* (2006.01)

(52) U.S. Cl.
USPC ............ 436/110; 436/106; 436/164; 436/166

(58) Field of Classification Search
USPC .................................. 436/106, 110, 164, 166
See application file for complete search history.

(56) References Cited

U.S. PATENT DOCUMENTS

| | | | | |
|---|---|---|---|---|
| 4,003,706 A | * | 1/1977 | Szekely | 436/110 |
| 5,366,900 A | * | 11/1994 | Conboy et al. | 436/107 |
| 5,668,014 A | * | 9/1997 | Aoki et al. | 436/110 |
| 5,858,792 A | * | 1/1999 | Fanning et al. | 436/52 |
| 5,993,742 A | * | 11/1999 | Binz et al. | 436/110 |
| 6,051,436 A | * | 4/2000 | Reagen et al. | 436/106 |
| 7,485,464 B2 | * | 2/2009 | Platano et al. | 436/110 |
| 2006/0121620 A1 | * | 6/2006 | Bhandari | 436/110 |
| 2006/0121621 A1 | * | 6/2006 | Bhandari | 436/110 |

OTHER PUBLICATIONS

Torro, I. G. et al, Analytica Chimica Acta 1998, 366, 241-249.*
Cerda, A. et al, Analytica Chimica Acta 1998, 371, 63-71.*
Legnerova, Z. et al, Water Research 2002, 36, 2777-2783.*
Nova, A. Analytica Chimica Acta 2003, 476, 131-139.*
Feres, M. A. et al, Talanta 2005, 68, 422-428.*

(Continued)

*Primary Examiner* — Arlen Soderquist
(74) *Attorney, Agent, or Firm* — Samuel M. Freund; Cochran Freund & Young LLC

(57) ABSTRACT

Methods for determining the concentration of nitrates in several types of water samples by photochemical reduction without the use of toxic materials such as cadmium or hydrazine, and having an approximately 100% reduction efficiency are described. A water sample mixed with a buffered aqueous solution including ammonium salts and EDTA is irradiated using ultraviolet light having wavelengths effective for photochemical conversion of nitrate and nitrite ions ($NO_x$) to detectable species. The resulting species may be quantitatively determined by diazotization using sulfanilamide followed by coupling with N-(1-napthyl)ethylenediamine dihydrochloride which produces a water-soluble azo dye having a magenta color which may be colorimetrically measured at 540 nm from which the nitrate and nitrite concentration in the sample is determined. Nitrite present in the original sample may be colorimetrically analyzed using an unphotolyzed sample and the reaction with sulfanilamide followed by coupling with N-(1-napthyl)ethylenediamine dihydrochloride. When the nitrite concentration is subtracted from the total of the nitrate and nitrite concentration, the sample nitrate may be determined.

26 Claims, 2 Drawing Sheets

(56) References Cited

OTHER PUBLICATIONS

Lima, M. J. R. et al, International Dairy Journal 2006, 16, 1442-1447.*

Fanning, James C., "The chemical reduction of nitrate in aqueous solution," Coordination Chemistry Reviews, 2000, pp. 159-179.

Calatayud, J. Martinez et al., "Multi-insertion of small controlled volumes of solutions in a flow assembly for determination of nitrate (photoreduction) and nitrite with proflavin sulfate," Analyst, Mar. 1998, vol. 123, pp. 429-434.

Motomizu, Shoji et al., "Photo-induced reduction of nitrate to nitrite and its application to the sensitive determination of nitrate in natural waters," Analytica Chimica ACTA, vol. 308, 1995, pp. 406-412.

Takeda, Kazuhiko et al., "Determination of nitrate in waters with the photo-induced conversion of nitrate to nitrite," Analytica Chimica Acta, 276, 1993, pp. 25-32.

Chow, Christopher et al., Development of Low Cost On-line Monitoring Package to Improve Chloramination Control: Stage 1 Ammonia Analyser Development—Laboratory Assessment and Project Overview, Research Report No. 44, The Cooperative Research Centre for Water Quality and Treatment, (2007), pp. 1-50.

Great Lakes National Program Office—U.S. Environmental Protection Agency, "Standard Operating Procedure for Nitrate—Nitrite in Lake Water (QuikChemFIA+8000 Method)," Sampling and Analytical Procedures for GLNPO's Open Lake Water Quality Survey of the Great Lakes—Chapter 2: Nutrient Parameters, Dec. 2002, pp. 1-9.

Young, Courtney, Final Report—Photoassisted Electron Transfer Reactions of Application to Mine Wastewater Cleanup: Nitrate and Cyanide, Mine Waste Technology Program, Activity IV, Project 3, pp. 1-26.

Bilski, P. et al., "Photooxidation of Organic and Inorganic Substrates during UV Photolysis of Nitrite Anion in Aqueous Solution," J. Am. Chem. Soc. 1992, 114- pp. 549-556.

Tennakone, K. et al., "Photocatalytic Oxidation of Nitrite in Water to Nitrate," Environmental Pollution 57, 1989, pp. 299-305.

Sato, Tsugio et al., "Photochemical Reduction of Nitrate to Ammonia Using Layered Hydrous Titanate/Cadmium Sulphide Nanocomposites," J. Chem. Tech Biotechnol. 1996, 67. pp. 345-349.

Nelieu, S. et al., "Nitrite and nitrate induced photodegradation of monolinuron in aqueous solution," Environ. Chem. Lett. 2004, pp. 83-87.

Spokes, Lucinda et al., "Photochemically induced redox reactions in seawater, II. Nitrogen and iodine," Marine Chemistry 54, 1996, pp. 1-10.

* cited by examiner

DETERMINATION OF NITRATE/NITRITE CONCENTRATION IN WATER BY QUANTITATIVE PHOTOCHEMICAL REDUCTION USING NH₄CL AND EDTA

CROSS-REFERENCE TO RELATED APPLICATIONS

The present application claims the benefit of Provisional Patent Application Ser. No. 61/232,298 for "Determination of Nitrate Concentration in Water by Photochemical Reduction" by Scott A. Tucker and Lynn M. Egan, filed on Aug. 7, 2009, which provisional application is hereby incorporated by reference herein for all that it discloses and teaches.

FIELD OF THE INVENTION

The present invention relates generally to the detection of nitrates and nitrites in water and, more particularly to the quantitative determination of nitrates and nitrites in water without the requirement of cadmium, hydrazine or other toxic materials.

BACKGROUND OF THE INVENTION

Nitrates are major components in fertilizers, explosives and by-products of certain detonated explosives, and may enter discharge waters from the mining and agricultural industries. Nitrates promote the growth of algae and other plant life in slow-moving streams, rivers and lakes resulting in increased turbidity and oxygen depletion, eventually destroying life in such waterways. Large quantities of nitrates in drinking water are harmful to animals and humans as a result of conversion to nitrites by gastrointestinal bacteria since hemoglobin reacts with nitrites in place of oxygen, thereby causing respiratory failure. Methods for removing nitrates from solutions include ion exchange, reverse osmosis and biological methods, which are expensive and nondestructive, thereby generating wastes that must be treated.

Determination of nitrate inn concentration in water is important in environmental and marine chemistry. Nitrate levels in soil are also an important parameter for agriculture. Nitrite ions generated by reduction of nitrate ions may be detected by spectrophotometric measurement. Such reduction has been achieved by passing sample solutions through a copperized cadmium column; however, the eluted solutions contain cadmium and copper which must be eliminated before discharge. An ammonium chloride and disodium ethylenediaminetetraacetic acid buffer having a pH of about 8.5 has been used as a carrier solution for sample solutions. Hydrazine has also been utilized in the reduction step. Nitrite in the original sample may be determined by removing the cadmium column.

Photolysis of nitrates to nitrites or ammonia is known. Water denitrification by stopping the reduction of nitrate at nitrite, lowering the pH of the water, and air sparging the unstable nitrite from of the water has been described. Nitrate photoreduction in sample solutions containing humic acid or hydrazine at a pH of 10 and continuously sparged with argon gas to eliminate oxygen has been performed, and analyzed using an ion chromatograph. The nitrate reduction was found not to exceed 21%. A two-stage process for decreasing the nitrate content of water by reducing nitrates to nitrogen has been reported: photochemical reduction to nitrite; and reduction of nitrite to nitrogen using amidosulphuric (sulfamic) acid.

Spectrophotometric determination of nitrate in samples of river, inland sea and open sea water by photo-induced reduction of nitrate to nitrite in a phosphate-buffered carrier solution at pH 8 flowed through a quartz coil irradiated using a mercury lamp has been studied. The conversion efficiency of nitrate was approximately 50%.

Improved photoreduction efficiency has been achieved by flowing samples in a phosphate-buffer carrier solution having a pH of 7.0 to which the activators ethylenediaminetetraacetic acid (EDTA) or diethylenetriamine-N,N,N',N'',N''-pentaacetic acid (DTPA) have been added through poly(tetrafluoroethlyene) (PTFE) tubing irradiated with a mercury lamp. The reduction efficiency was found to be 70-84%, with higher conversion efficiencies being obtained using DTPA as the activator.

Total nitrite (reduced nitrate plus any nitrite originally existing in the sample) may be determined by diazotizing with sulfanilamide followed by coupling with N-(1-naphthyl) ethylenediamine dihydrochloride. The resulting water soluble azo dye has a magenta color which may be read at 540 nm, and is known as the Griess test.

SUMMARY OF THE INVENTION

Accordingly, it is an object of the present invention to provide a method for quantitatively determining nitrate and nitrite ions present in a water sample.

Another object of the invention is to provide a method for quantitatively determining nitrate and nitrite ions present in a water sample without requiring the use of hazardous materials.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method for determining the nitrate and nitrite concentration in a sample of water, hereof, includes: mixing the sample with an aqueous solution containing chosen quantities of ammonium chloride and ethylenediamine tetraacetic acid; adjusting the pH to a chosen value; quantitatively photoreducing the nitrate and nitrite to detectable species; and detecting the nitrogen compounds generated by the step of photoreduction, from which the nitrate and nitrite concentrations are determined.

In another aspect of the invention in accordance with its objects and purposes the method for determining the nitrate and nitrite concentration in a water sample, includes: mixing the sample with an aqueous solution consisting essentially of chosen quantities of ammonium chloride and ethylenediamine tetraacetic acid; adjusting the pH to a chosen value; quantitatively photoreducing the nitrate and nitrite to detectable species; and detecting the detectable species generated by the step of photoreduction, whereby the nitrate and nitrite concentration is determined.

Benefits and advantages of the present invention include, but are not limited to, providing an efficient method for quantitatively determining nitrate and nitrite in a water sample using the photoreduction thereof to detectable entities without requiring the use of hazardous materials, and having an approximately 100% reduction efficiency.

BRIEF DESCRIPTION OF THE DRAWING

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Figure 1:
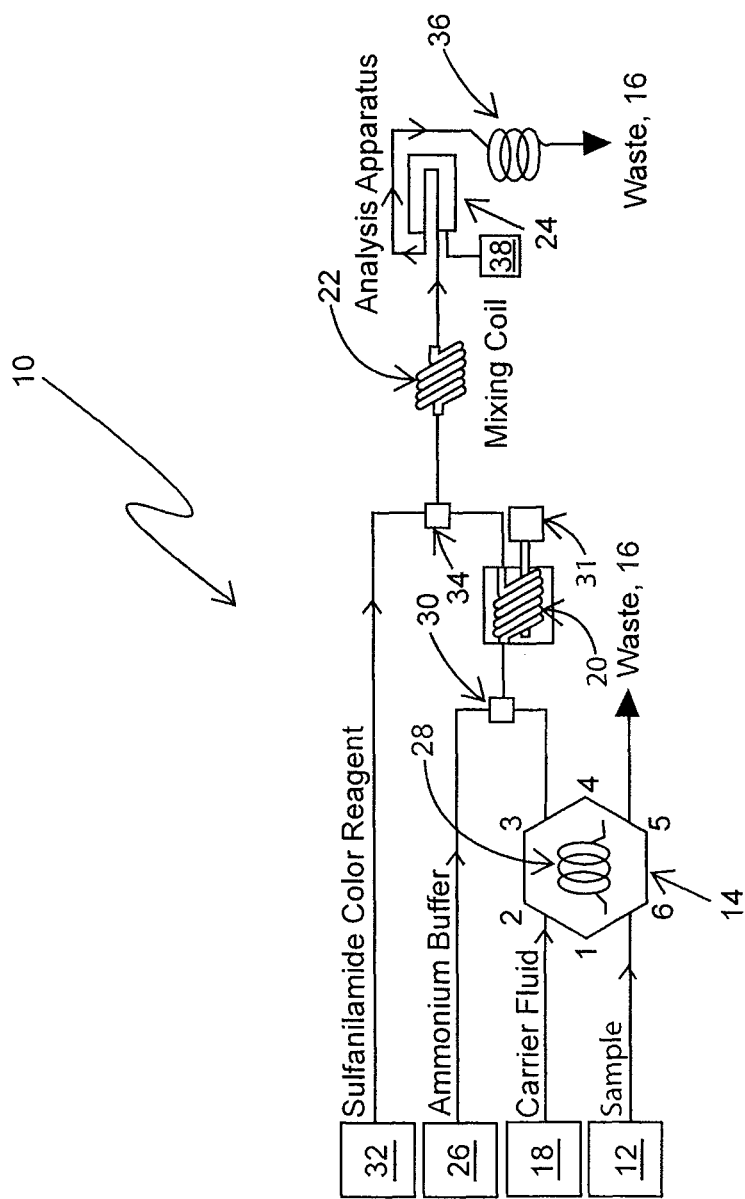
FIG. 1 is a schematic representation of an apparatus effective for practicing embodiments of the method of the present invention.

Briefly, the present invention includes apparatus and methods for determining the concentration of nitrates and nitrites in water by photochemical reduction without the use of toxic materials such as cadmium or hydrazine, and having an approximately 100% reduction efficiency.

Nitrates and nitrites in an aqueous sample are quantitatively photo-converted to nitrogen species detectable by traditional colorimetric methods by irradiating a flowing sample with UV radiation. The extent of the reduction is managed utilizing ethylenediamine tetraacetic acid (EDTA) in the buffer allowing for the conversion efficiency of the nitrates and nitrites into species detectable using traditional colorimetric methods to reach approximately 100% (quantitative conversion) while avoiding over-reducing the nitrates and nitrites to oxidation states that cannot be so detected.

In one embodiment of the invention, the determination of $NO_3^-$ and $NO_2^-$ in samples may be accomplished by utilizing a flow injection apparatus (FIA) having at least 2 channels. Combined $NO_3^-$ and $NO_2^-$ ($NO_x$) may be analyzed on the first channel, and $NO_2^-$ on the second channel. By subtracting the $NO_2^-$ concentration from the $NO_x$ concentration, $NO_3^-$ can be determined. The water sample is combined with a buffered carrier system including chosen quantities of ammonium salts and EDTA at a selected pH, and flowed through Polytetrafluoroethylene (PTFE) tubing irradiated by a low-pressure mercury lamp operating at about 254 nm. A photoreduction efficiency of about 100% was observed. The PTFE tubing may be coiled around the lamp to increase utilization of lamp output. Quartz tubing or vessels may be used, as may other types of UV transparent and unreactive tubing or vessels. The generated detectable nitrogen concentration may then be determined by diazotizing with sulfanilamide followed by coupling with N-(1-napthyl)ethylenediamine dihydrochloride which produces a water-soluble azo dye having a magenta color which may be read at 540 nm using a colorimeter, as an example, and from which the concentration of nitrate in the sample is determined. An unphotolyzed sample may be analyzed by this procedure to determine the amount of nitrite present in the original sample.

A static (nonflowing) sample may also be analyzed in accordance with embodiments of the invention.

Since there are no toxic compounds used in this chemical reaction, waste solutions may be disposed of in normal drainage systems. The efficiency of reduction of $NO_3$ to $NO_2$ in accordance with the teachings of embodiments of the present invention is similar to that for the enzymatic nitrate reductase method; however, the chemical reaction for the UV reduction may be completed in a shorter time period, is less complicated and is less expensive.

The term "water," as used herein, may be rain water, ground water, drinking water, industrial process water, industrial effluent, pool water, sewage, sludge, grey water, spring water, aquifer water, sea water, tap water, irrigation water, agricultural feed water, glacial melt water, treated water, untreated water, steam or atmospheric humidity, aqueous solutions used to extract nitrates from soil samples, and virtually any other sample containing $H_2O$ for which it is desired to know the concentration of nitrates and/or nitrites can be tested. Specific test procedures will be set forth in the EXAMPLES.

Reference will now be made in detail to the embodiments of the invention, examples of which are illustrated in the accompanying drawings. Turning to FIG. 1, a schematic representation of an embodiment of flow injection apparatus, 10, effective for practicing embodiments of the method of the present invention is shown. As stated hereinabove, the method hereof may also be practiced using static (non-flowing) samples and reagents. Aqueous sample, 12, which may be generated from a variety of sources, is pumped into port 6 of 2-state, 6 port injection valve, 14, and may exit port 5 of valve 14 for disposal, 16, after passing through ports 1 and 4. Carrier fluid, 18, is pumped into port 2 of valve 14, through ports 1, 4, and 3, through sample cell, 20, which may be exposed to UV radiation, mixing coil, 22, and analysis cell, 24, after which it is disposed of 16. The carrier fluid may be helium degassed deionized water, as an example. Mixing coil 22 may be 70 mm in length, as an example. Ammonium buffer, 26, described in detail in the EXAMPLES is pumped into the effluent from port 3 in mixing tee, 30. When a measurement is made, sample 12 is flowed into tubing, 28, between ports 1 and 4 and swept by carrier fluid 18 out of tubing 28 through port 3 into sample cell 20. Nitrates and nitrites contained in sample 12 are photoreduced to detectable species in cell 20 by radiation from UV source, 31. Sulfanilamide reagent, 32, to be described in detail in the EXAMPLES is added to the photolysis solution in mixing tee, 34, the resulting solution is mixed in mixing coil 22, and analyzed in cell 24. A backpressure coil, 36, including 100 cm of 0.5 mm inner diameter tubing, may be provided to reduce formation of bubbles in irradiation cell 20.

Photoreduction of nitrates and nitrites in water samples was achieved by passing samples mixed with the ammonium-buffered carrier solution using a Ushio G6T5 Low Pressure Germicidal Lamp having a spectral distribution centered around 254 nm and an output of 1.8 W through PTFE tubing (580 cm of Zeus 0.8 mm inner diameter PTFE tubing) disposed in the vicinity of lamp 31, or coiled around lamp 31 and held against the lamp with aluminum foil. The aluminum foil (not shown in FIG. 1) also acts as a reflector to increase the efficiency of the irradiation. By photoreducing the sample using ultraviolet light at 254 nm (254 nm mercury germicidal lamp), and utilizing chosen concentrations of EDTA and ammonium chloride in the ammonium buffer, the reduction efficiency can be adjusted to be approximately quantitative (90%-100%). Clearly, any source of ultraviolet radiation effective for photoreducing nitrates and nitrites to detectable entities may be used. Moreover, as stated hereinabove, a quartz or other UV transparent vessel may be used for the photoreduction step for flowing or static samples.

The reduced $NO_x$ species (reduced nitrate and nitrite) may then be determined by diazotizing with the sulfanilamide reagent which contains hydrochloric acid, sulfanilamide and N-(1-naphthyl)ethylenediamine dihydrochloride at a pH less than 2. The resulting water-soluble dye has magenta color which may be colorimetrically or spectrophotometrically analyzed at 540 nm in analysis cell 24, and analyzed and recorded using apparatus, 38. As mentioned, an unphotolyzed sample may be analyzed using the Griess reaction to determine the quantity of nitrite in the original sample. Other nitrite detection methods may also be employed, such as ion chromatography, as an example.

Aqueous samples to be analyzed for nitrates and nitrites may have various ionic compositions; therefore, the concentration of the ammonium chloride/EDTA buffer solution and the pH thereof may require adjustment to suit these compositions in order to achieve approximately 100% photoreduction efficiency. It should be mentioned that the EDTA serves the dual function of chelating divalent cations present in the samples. For illustrative purposes, and not intended to limit the scope of the present method, the following EXAMPLES provide additional details of the solutions effective for producing approximately 100% photoreduction of sample nitrates and nitrites into detectable species, and their use.

EXAMPLE 1

Reagents for General Water Analyses

Deionized (DI) water (10 MΩ) is used for all solutions. To prevent bubble formation during analysis, all solutions except the standard solutions are degassed using helium.

A. 15 N Sodium Hydroxide: by volume, add 150 g of NaOH to 250 mL or g of deionized (DI) water; swirl until dissolved; cool; and store in a plastic bottle.

B. Ammonium Chloride buffer, pH 8.0±0.1:

1. by volume, 85.0 g ammonium chloride ($NH_4Cl$) and 4.0 g of disodium ethylenediamine tetraacetic acid dihydrate ($Na_2EDTA \cdot 2H_2O$) are dissolved in about 800 mL of DI water in a 1 L volumetric flask; the mixture is diluted to 1 L, and mixed; and the pH is adjusted to 8.0 using the 15 N sodium hydroxide solution; or 2. by weight, 85.0 g of ammonium chloride ($NH_4Cl$), and 4.0 g disodium ethylenediamine tetraacetic acid dihydrate ($Na_2EDTA \cdot 2H_2O$) are added to 938 g of DI water in a tared container; the mixture is shaken or stirred until the solids are dissolved; and the pH is adjusted to 8.0±0.1 with 15 N sodium hydroxide solution.

Ammonium chloride has been found to occasionally contain significant nitrate contamination. An alternative preparation includes:

a. by volume, 105 mL of concentrated hydrochloric acid (HCl), 95 mL ammonium hydroxide ($NH_4OH$), and 4.0 g of disodium EDTA, are dissolved in 500 mL of DI water in a 1 L volumetric flask; the mixture is diluted to 1 L, and inverted to mix; and the pH is adjusted to 8.0±0.1 using HCl or 15 N NaOH solution; or b. by weight, 126 g concentrated hydrochloric acid (HCl), 85 g ammonium hydroxide ($NH_4OH$), and 4.0 g disodium EDTA are dissolved in 800 g of DI water in a tared container; and the pH is adjusted to 8.0±0.1 with HCl or 15 N NaOH solution.

C. Sulfanilamide color reagent:

By volume: about 600 mL of DI water, 100 mL of concentrated hydrochloric acid (37% HCl), 10.0 g sulfanilamide ($C_6H_8N_2O_2S$), and 1.0 g N-(1-naphthyl)ethylenediamine dihydrochloride (NED) are placed in a 1 L volumetric flask; the mixture is shaken to wet the solids, and stirred for 20 min. to dissolve solids; and diluted to 1 L with DI water, inverted to mix; and stored in a dark bottle. The solution is discarded when dark pink.

D. Standards:

1. Stock Nitrate Standards (200 mg N/L and 20 mg N/L) were prepared using potassium nitrate and DI water (such solutions were found to be stable for about six months); and 2. Stock Nitrite Standards (200 mg N/L and 20 mg N/L) were prepared using sodium or potassium nitrite and DI water (such solutions were found to be stable for 3-5 days).

The pH and the EDTA concentration of the buffer affect the percent reduction of nitrate and nitrite to detectable forms of nitrogen in water samples having concentrations between about 0.05 and about 20 mg N/L as $NO_3^-$ and/or $NO_2^-$, and is checked and adjusted daily, if required.

Further, different light output from different UV lamps, and differences in quality or age of reagents, the amount of EDTA in the buffer may have to be adjusted to reach approximately 100% reduction efficiency: (a) If the $NO_2^-$ concentration is higher than the $NO_3^-$ concentration, additional EDTA may be added to the buffer to reduce the $NO_2^-$ concentration to the same level as $NO_3^-$; and (b) If the $NO_3^-$ concentration is higher than the $NO_2^-$ concentration, the amount of EDTA in the buffer may be reduced to obtain equality. If the concentration of $NH_4Cl$ is sufficiently high, and the pH is adjusted to 8.0±0.1, only the EDTA need be adjusted.

To test the reduction efficiency, a liter of buffer is prepared with 85 g of $NH_4Cl$ and the pH adjusted to 8±0.1. To an approximately 250 mL aliquot, the appropriate quantity of EDTA is added to either increase or decrease the $NO_3^-$ signal. If the efficiency is between about 50-60%, approximately 2 g of EDTA/L was observed to bring the efficiency to approximately 100%, while if the efficiency is between about 20-25%, approximately 1 g of EDTA/L was found to suffice. This is in addition to the 4 g of EDTA already present.

Most cations and anions commonly found in drinking, surface and wastewaters do not interfere with the determination of nitrate. Low results may be obtained for samples that contain high concentrations of iron, copper or other metals. However, EDTA is added to the buffer also to reduce this interference. Further, samples having high concentrations of organics (~90 mg/L TOC) may produce a negative peak during the UV-conversion. To eliminate this interference, the sample is diluted with DI water to reduce the TOC concentration. If nitrate/nitrite concentration is too low to permit dilution, approximately 500 mg of Bio-Beads® S-X12 Geo1 (Bio-Rad part no. 152-3650) to a 10 mL sample aliquot, which is homogenized and filtered or centrifuged to remove the polymer from the sample. Other substance may be used to remove organic materials in the sample. Turbidity may be substantially reduced by filtration through a 0.45 μm pore diameter membrane filter prior to analysis.

EXAMPLE 2

Reagents for Sea and Brackish Waters

Deionized (DI) water (10 MΩ) is used for all solutions. To prevent bubble formation during analysis, all solutions except the standard solutions are degassed using helium.

A. 15 N Sodium Hydroxide: by volume, add 150 g of NaOH to 250 mL or g of deionized (DI) water; swirl until dissolved; cool; and store in a plastic bottle.

B. Ammonium Chloride buffer, pH 8.2±0.1:

1. by volume: dissolve 85.0 g ammonium chloride ($NH_4Cl$) and, for high nitrate concentration ranges (water samples having concentrations between about 0.2 and about 20 mg N/L as $NO_3^-$ or $NO_2^-$) dissolve 10.0 g, and for low nitrate concentration ranges (water samples having concentrations between about 0.05 and about 5.0 mg N/L as $NO_3^-$ or $NO_2^-$) dissolve 15 g disodium ethylenediamine tetraacetic acid dihydrate ($Na_2EDTA \cdot 2H_2O$) in about 800 mL DI water in a 1

L volumetric flask; dilute to 1 L and invert to mix; and adjust the pH to 8.2±0.1 with 15 N sodium hydroxide solution prepared as described hereinabove.

2. by weight: add 85.0 g ammonium chloride ($NH_4Cl$) and, for the high concentration range, 10.0 g, and for the low concentration range, 15 g of disodium ethylenediamine tetraacetic acid dihydrate ($Na_2EDTA \cdot 2H_2O$) to 938 g of DI water in a tared container; shake or stir until dissolved; and adjust the pH to 8.2±0.1 with 15 N sodium hydroxide solution prepared as described hereinabove.

Alternative preparation of ammonium chloride buffer, where the ammonium chloride contains significant nitrate contamination:

a. by volume: to 500 mL of DI water, add 105 mL of concentrated hydrochloric acid (HCl), 95 mL of ammonium hydroxide ($NH_4OH$), for high concentrations, and 10.0 g, and for low concentrations, and 15 g of disodium EDTA in a 1 L volumetric flask; mix to dissolve the solids and dilute to 1 L using DI water; invert to mix; and adjust the pH to 8.2±0.1 with HCl or 15 N NaOH solution;

b. by weight: to 800 g of DI water, add 126 g of concentrated hydrochloric acid (HCl), 85 g ammonium hydroxide ($NH_4OH$); for the high concentration range, 10.0 g, and for the concentration range 15 g of disodium EDTA in a tared container; stir to dissolve the solids; and adjust the pH to 8.2±0.1 with HCl or 15 N NaOH solution.

C. Sulfanilamide color reagent:

By volume: about 600 mL of DI water, 100 mL of concentrated hydrochloric acid (37% HCl), 10.0 g sulfanilamide ($C_6H_8N_2O_2S$), and 1.0 g N-(1-naphthyl)ethylenediamine dihydrochloride (NED) are placed in a 1 L volumetric flask; the mixture is shaken to wet the solids, and stirred for 20 min. to dissolve solids; diluted to 1 L with DI water; inverted to mix; and stored in a dark bottle. The solution is discarded when dark pink.

D. Artificial Seawater:

1. By volume: about 600 mL of DI water, 29.3 g of sodium chloride (NaCl), 9.4 g of magnesium sulfate heptahydrate ($MgSO_4 \cdot 7 H_2O$), and 0.22 g of sodium bicarbonate ($NaHCO_3$) are added to a 1 L volumetric flask; mixed to dissolve the solids; and diluted to 1 L with DI water.

2. By weight: 981 g of DI water, 29.3 g of sodium chloride (NaCl), 9.4 g of magnesium sulfate heptahydrate ($MgSO_4 \cdot 7 H_2O$) are added to a tared container. This solution is used to prepare the standards and adjust volumes.

E. Preparation of Standards:

1. Stock Nitrate Standards (200 mg N/L and 20 mg N/L) were prepared using potassium nitrate in artificial seawater (such solutions were found to be stable for about six months); and 2. Stock Nitrite Standards (200 mg N/L and 20 mg N/L) were prepared using sodium or potassium nitrite in artificial seawater (such solutions were found to be stable for 3-5 days).

The pH and the EDTA concentration of the buffer affect the percent reduction of nitrate to nitrite in brackish water and seawater having concentrations between 0.05 mg N/L and 20 mg N/L as $NO_3^-$ and/or $NO_2^-$. The pH of the buffer may be checked and, if necessary, adjusted daily.

Further, due to different light output from different UV lamps, and differences in quality or age of reagents, the amount of EDTA in the buffer may have to be adjusted to reach approximately 100% reduction efficiency: (a) If the $NO_2^-$ concentration is higher than the $NO_3^-$ concentration, additional EDTA may be added to the buffer to reduce the $NO_2^-$ concentration to the same level as $NO_3^-$; and (b) If the $NO_3^-$ concentration is higher than the $NO_2^-$ concentration, the amount of EDTA in the buffer may be reduced.

To test the reduction efficiency, a liter of buffer is prepared with the 85 g of $NH_4Cl$ and the pH adjusted to 8.2±0.1. To an approximately 250 mL aliquot, the appropriate quantity of EDTA is added to either increase or decrease the $NO_3^-$ signal. If the efficiency is between about 50-60%, approximately 2 g of EDTA/L was observed to bring the efficiency to 100%, while if the efficiency is between about 20-25%, approximately 1 g of EDTA/L was found to suffice. If the concentration of $NH_4Cl$ is sufficiently high, and the pH is adjusted to 8.2±0.1, only the EDTA need be adjusted Low results may be obtained for samples that contain high concentrations of iron, copper or other metals. However, EDTA is added to the buffer to reduce this interference. Further, samples having high concentrations of organics (~90 mg/L TOC) may produce a negative peak during the UV-conversion. To eliminate this interference, the sample is diluted with Artificial Seawater to reduce the TOC concentration. If nitrate/nitrite concentration is too low to permit dilution, approximately 500 mg of Bio-Beads® S-X12 Geol (Bio-Rad part no. 152-3650) to a 10 mL sample aliquot, which is homogenized and filtered or centrifuged to remove the polymer from the sample. Other substance may be used to remove organic materials in the sample. Turbidity may be substantially reduced by filtration through a 0.45 μm pore diameter membrane filter prior to analysis.

EXAMPLE 3

Reagent Formulations for 2 M KCl Extracts (Common for Soil Analyses, where the KCl Solution is used to Extract Nitrates from the Soil Sample, as an Example)

Deionized (DI) water (10 MΩ) is used for all solutions. To prevent bubble formation during analysis, all solutions except the standard solutions are degassed using helium.

A. 15 N Sodium Hydroxide: by volume, add 150 g of NaOH to 250 mL or g of deionized (DI) water; swirl until dissolved; cool; and store in a plastic bottle.

B. Ammonium Chloride Buffer Solution having a pH of 8.2±0.1:

1. by volume: dissolve 85.0 g ammonium chloride ($NH_4Cl$) and 5.5 g of disodium ethylenediamine tetraacetic acid dihydrate ($Na_2EDTA \cdot 2H_2O$) in about 800 mL of DI water in a 1 L volumetric flask; dilute to 1 L; invert to mix; and adjust the pH to 8.2±0.1 with 15 N sodium hydroxide solution;

2. by weight: add 85.0 g ammonium chloride ($NH_4Cl$) and 5.5 g of disodium ethylenediamine tetraacetic acid dihydrate ($Na_2EDTA.2H_2O$) to 938 g of DI water in a tared container; shake or stir until the solids are dissolved; and adjust the pH to 8.2 with 15 N sodium hydroxide solution.

ACS grade ammonium chloride has been found to contain nitrate contamination. An alternative recipe for the ammonium chloride buffer is:

a. by volume: to 500 mL of DI water, add 105 mL of concentrated hydrochloric acid (HCl), 95 mL of ammonium hydroxide ($NH_4OH$), and 5.5 g of disodium EDTA in a 1 L volumetric flask; mix to dissolve the solids; dilute to 1 L; invert to mix; and adjust the pH to 8.2±0.1 with HCl or 15 N NaOH solution;

b. by weight: to 800 g DI water, add 126 g concentrated hydrochloric acid (HCl), 85 g ammonium hydroxide ($NH_4OH$), and 5.5 g disodium EDTA in a tared container; stir to dissolve; and adjust the pH to 8.2±0.1 with HCl or 15 N NaOH.

C. Sulfanilamide color reagent:

By volume: about 600 mL of DI water, 100 mL of concentrated hydrochloric acid (37% HCl), 10.0 g sulfanilamide ($C_6H_8N_2O_2S$), and 1.0 g N-(1-naphthyl) ethylenediamine dihydrochloride (NED) are placed in a 1 L volumetric flask; the mixture is shaken to wet the solids, stirred for 20 min. to dissolve solids; and diluted to 1 L with DI water; inverted to mix; and stored in a dark bottle. The solution is discarded when dark pink.

D. 2 M Potassium Chloride Solution; Carrier and Standards Diluent:

1. By volume: 149 g of potassium chloride (KCl) is dissolved in about 800 mL of DI water in a 1 L volumetric flask; diluted to 1 L with DI water; and inverted to mix.

2. By weight: 149 g of potassium chloride (KCl) is dissolved in 1000 g of DI water in a tared container; and inverted to mix. This solution is the same concentration as the KCl extraction solution, and is used to make up the standards and the carrier solutions.

E. Preparation of Standards:

1. Stock Nitrate Standards (200 mg N/L and 20 mg N/L) were prepared using potassium nitrate in potassium chloride solution (such solutions were found to be stable for about six months); and 2. Stock Nitrite Standards (200 mg N/L and 20 mg N/L) were prepared using sodium or potassium nitrite in potassium chloride solution (such solutions were found to be stable for 3-5 days).

The pH and the EDTA concentration of the buffer affect the percent reduction of nitrate to nitrite with 2 M KCl soil extraction solutions having concentrations between about 0.2 and about 20 mg N/L as $NO_3$ and/or $NO_2$, and may be checked and, if necessary adjusted, daily. A nitrite standard may be run during sample tests to ensure that the nitrate is being fully reduced.

Further, different light output from different UV lamps, and differences in quality or age of reagents, the amount of EDTA in the buffer may have to be adjusted to reach approximately 100% reduction efficiency: (a) If the $NO_2^-$ concentration is higher than the $NO_3^-$ concentration, additional EDTA may be added to the buffer to reduce the $NO_2^-$ concentration to the same level as $NO_3^-$; and (b) If the $NO_3^-$ concentration is higher than the $NO_2^-$ concentration, the amount of EDTA in the buffer may be reduced.

To test the reduction efficiency, a liter of buffer is prepared with the 85 g of $NH_4Cl$ and the pH adjusted to 8.2±0.1. To an approximately 250 mL aliquot, the appropriate quantity of EDTA is added to either increase or decrease the $NO_3^-$ signal. If the efficiency is between about 50-60%, approximately 2 g of EDTA/L was observed to bring the efficiency to approximately 100%, while if the efficiency is between about 20-25%, approximately 1 g of EDTA/L was found to suffice. If the concentration of $NH_4Cl$ is sufficiently high, and the pH is adjusted to 8.2±0.1, only the EDTA need be adjusted Low results may be obtained for samples that contain high concentrations of iron, copper or other metals. However, EDTA is added to the buffer to reduce this interference. Further, samples having high concentrations of organics (~90 mg/L TOC) may produce a negative peak during the UV-conversion. To eliminate this interference, the sample is diluted with potassium chloride solution to reduce the TOC concentration. If nitrate/nitrite concentration is too low to permit dilution, approximately 500 mg of Bio-Beads® S-X12 Geol (Bio-Rad part no. 152-3650) to a 10 mL sample aliquot, which is homogenized and filtered or centrifuged to remove the polymer from the sample. Other substances may be used to remove organic materials in the sample. Turbidity may be substantially reduced by filtration through a 0.45 µm pore diameter membrane filter prior to analysis.

For the samples of EXAMPLES 1-3, exemplary of flow rates employed using the apparatus illustrated in FIG. 1 include: 2.47 ml/min. for the carrier fluid, 0.94 ml/min. for the ammonium buffer, prepared as described hereinabove, and 0.76 ml/min. for the sulfanilamide color reagent, prepared as described hereinabove. The carrier fluid may be flowed such that the apparatus is flushed 2-3 times between colorimetric measurements.

These flow rates translate to 0.38±0.02 mL of ammonium buffer and 0.22±0.02 mL of sulfanilamide color reagent to 1 mL of sample for a static system.

Figure 2:
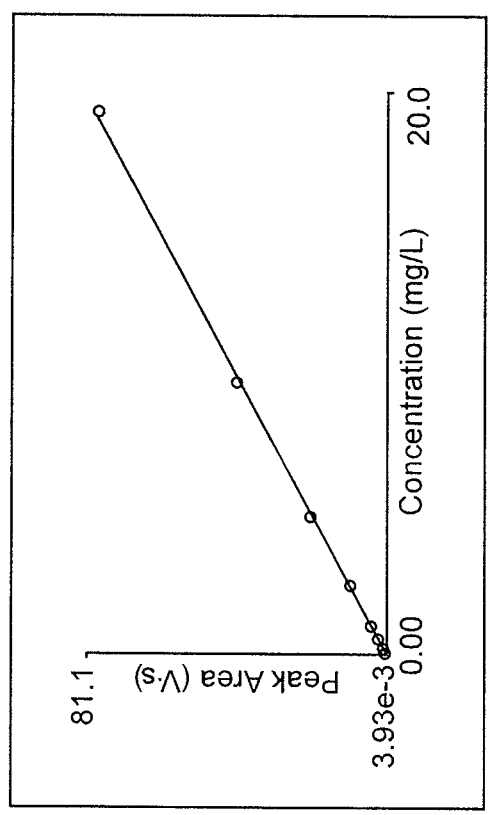
FIG. 2 is a graph of the peak area in volt·seconds of the measured photolyzed nitrate or nitrite after diazotizing with sulfanilamide followed by coupling with N-(1-naphthyl)ethylenediamine dihydrochloride, as a function of total nitrogen concentration in mg/L in water samples.

FIG. 2 is a sample analytical curve for the detection of nitrates in water samples using the solutions set forth in EXAMPLE 1, hereinabove, showing a graph of the peak area in volt·seconds of the measured photolyzed nitrate or nitrite after diazotizing with sulfanilamide followed by coupling with N-(1-naphthyl)ethylenediamine dihydrochloride, as a function of total nitrogen concentration in mg/L. The data points are represented by circles, and the line represents the best fit straight line therethrough. The resulting detection limits are approximately 0.005 mg N/L for water samples, approximately 0.006 mg N/L for brackish water and seawater, and approximately 0.015 mg N/L for 2 M KCl soil extracts.

The TABLE shows concentration ratios of nitrate ions to nitrite ions and the measured total nitrogen concentration for water samples. As may be observed from the TABLE, the measured concentration remains approximately constant over the range of nitrate to nitrite concentration ratios investigated.

TABLE

| Nitrogen Compound Ratio | Concentration (mg N/L) | Nitrogen Compound Ratio | Concentration (mg N/L) |
|---|---|---|---|
| 1 ppm $NO_2^-$ + 9 ppm $NO_3^-$ | 10.2 | 6 ppm $NO_2^-$ + 4 ppm $NO_3^-$ | 10.5 |
| 2 ppm $NO_2^-$ + 8 ppm $NO_3^-$ | 10.2 | 7 ppm $NO_2^-$ + 3 ppm $NO_3^-$ | 10.7 |
| 3 ppm $NO_2^-$ + 7 ppm $NO_3^-$ | 10.3 | 8 ppm $NO_2^-$ + 2 ppm $NO_3^-$ | 10.7 |
| 4 ppm $NO_2^-$ + 6 ppm $NO_3^-$ | 10.4 | 9 ppm $NO_2^-$ + 1 ppm $NO_3^-$ | 10.7 |
| 5 ppm $NO_2^-$ + 5 ppm $NO_3^-$ | 10.5 | | |

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining the nitrate and nitrite concentration in a water sample, comprising the steps of:
   mixing said sample with an aqueous solution comprising chosen quantities of ammonium chloride and ethylenediamine tetraacetic acid;
   adjusting the pH to a chosen value;
   quantitatively photoreducing the nitrate and nitrite to detectable species; and
   detecting the detectable species generated by said step of photoreduction, whereby the nitrate and nitrite concentration is determined.

2. The method of claim 1, further comprising the step of determining the nitrite concentration in said sample.

3. The method of claim 2, wherein said step of determining the nitrite concentration comprises the steps of:
mixing said sample with an aqueous solution comprising chosen quantities of ammonium chloride and ethylenediamine tetraacetic acid;
adjusting the pH to a chosen value; and
detecting the nitrite, whereby the concentration of nitrite is determined.

4. The method of claim 2, further comprising the step of subtracting said nitrite concentration from said nitrate and nitrite concentration to determine the nitrate concentration in said water sample.

5. The method of claim 2, wherein said step of detecting the nitrite comprises the steps of: mixing said water sample with a solution comprising hydrochloric acid, sulfanilamide and N-(1-naphthyl)ethylenediamine dihydrochloride at a pH less than 2, producing thereby a water-soluble azo dye; and measuring the absorption of said azo dye at 540 nm.

6. The method of claim 5, wherein said step of measuring is achieved using a colorimeter.

7. The method of claim 1, wherein said step of detecting the generated detectable species comprises the steps of: mixing the generated detectable species with a solution comprising hydrochloric acid, sulfanilamide and N-(1-naphthyl)ethylenediamine dihydrochloride at a pH less than 2, producing thereby a water-soluble azo dye; and
measuring the absorption of said azo dye at 540 nm.

8. The method of claim 7, wherein said step of measuring is achieved using a colorimeter.

9. The method of claim 1, wherein said step of quantitatively photoreducing the nitrate and nitrite to detectable species is achieved using a low-pressure mercury lamp having a spectral distribution centered around 254 nm.

10. The method of claim 9, wherein said sample mixed with said solution comprising chosen quantities of ammonium chloride and ethylenediamine tetraacetic acid at a chosen pH value is flowed through Polytetrafluoroethylene (PTFE) tubing disposed in the vicinity of said mercury lamp.

11. The method of claim 10, wherein said PTFE tubing is wrapped around said mercury lamp.

12. The method of claim 10, further comprising the step of increasing the backpressure of the mixture of said sample and said solution flowing through said PTFE tubing.

13. The method of claim 1, wherein said step of quantitatively photoreducing the nitrate and nitrite to detectable species is performed in the absence cadmium and hydrazine.

14. A method for determining the nitrate and nitrite concentration in a water sample, comprising the steps of:
mixing said sample with an aqueous solution consisting essentially of chosen quantities of water, ammonium chloride and ethylenediamine tetraacetic acid;
adjusting the pH to a chosen value;
quantitatively photoreducing the nitrate and nitrite to detectable species; and
detecting the detectable species generated by said step of photoreduction, whereby the nitrate and nitrite concentration is determined.

15. The method of claim 14, further comprising the step of determining the nitrite concentration in said sample.

16. The method of claim 15, wherein said step of determining the nitrite concentration comprises the steps of:
mixing said sample with an aqueous solution consisting essentially of chosen quantities of ammonium chloride and ethylenediamine tetraacetic acid;
adjusting the pH to a chosen value; and
detecting the nitrite, whereby the concentration of nitrite is determined.

17. The method of claim 15, further comprising the step of subtracting said nitrite concentration from said nitrate and nitrite concentration to determine the nitrate concentration in said water sample.

18. The method of claim 15, wherein said step of detecting the nitrite comprises the steps of: mixing said water sample with a solution comprising hydrochloric acid, sulfanilamide and N-(1-naphthyl)ethylenediamine dihydrochloride at a pH less than 2, producing thereby a water-soluble azo dye; and measuring the absorption of said azo dye at 540 nm.

19. The method of claim 18, wherein said step of measuring is achieved using a colorimeter.

20. The method of claim 14, wherein said step of detecting the generated detectable species comprises the steps of: mixing the generated detectable species with a solution comprising hydrochloric acid, sulfanilamide and N-(1-naphthyl)ethylenediamine dihydrochloride at a pH less than 2, producing thereby a water-soluble azo dye; and
measuring the absorption of said azo dye at 540 nm.

21. The method of claim 20, wherein said step of measuring is achieved using a colorimeter.

22. The method of claim 14, wherein said step of quantitatively photoreducing the nitrate and nitrite to detectable species is achieved using a low-pressure mercury lamp having a spectral distribution centered around 254 nm.

23. The method of claim 22, wherein said sample mixed with said solution comprising chosen quantities of ammonium chloride and ethylenediamine tetraacetic acid at a chosen pH value is flowed through Polytetrafluoroethylene (PTFE) tubing disposed in the vicinity of said mercury lamp.

24. The method of claim 23, wherein said PTFE tubing is wrapped around said mercury lamp.

25. The method of claim 23, further comprising the step of increasing the backpressure of the mixture of said sample and said solution flowing through said PTFE tubing.

26. The method of claim 14, wherein said step of quantitatively photoreducing the nitrate and nitrite to detectable species is performed in the absence of cadmium and hydrazine.

* * * * *